US012226148B2

(12) United States Patent
Gehl et al.

(10) Patent No.: US 12,226,148 B2
(45) Date of Patent: Feb. 18, 2025

(54) ELECTRODE ASSEMBLY FOR IMPROVED ELECTRIC FIELD DISTRIBUTION

(71) Applicant: Region Hovedstaden v/Herlev Hospital, Herlev (DK)

(72) Inventors: Karen Julie Gehl, Vanløse (DK); Faisal Mahmood, Ishøj (DK); Juan Luis Vásquez, København N (DK)

(73) Assignee: Region Hovedstaden v/Herlev Hospital, Herlev (DK)

( * ) Notice: Subject to any disclaimer, the term of this patent is extended or adjusted under 35 U.S.C. 154(b) by 820 days.

(21) Appl. No.: 17/290,882

(22) PCT Filed: Nov. 5, 2019

(86) PCT No.: PCT/EP2019/080198
§ 371 (c)(1),
(2) Date: May 3, 2021

(87) PCT Pub. No.: WO2020/094622
PCT Pub. Date: May 14, 2020

(65) Prior Publication Data
US 2021/0386474 A1 Dec. 16, 2021

(30) Foreign Application Priority Data
Nov. 5, 2018 (EP) .................................. 18204365

(51) Int. Cl.
*A61N 1/32* (2006.01)
*A61B 18/12* (2006.01)
*A61B 18/14* (2006.01)
*A61N 1/04* (2006.01)
*A61B 18/00* (2006.01)

(52) U.S. Cl.
CPC ...... *A61B 18/1482* (2013.01); *A61B 18/1206* (2013.01); *A61N 1/0416* (2013.01);
(Continued)

(58) Field of Classification Search
CPC .................. A61N 1/0416; A61N 1/327; A61B 2018/00613
See application file for complete search history.

(56) References Cited

U.S. PATENT DOCUMENTS

| 5,873,849 A | 2/1999 | Bernard |
| 6,014,584 A * | 1/2000 | Hofmann ............... A61N 1/327 607/116 |

(Continued)

FOREIGN PATENT DOCUMENTS

| EP | 1494752 A0 | 1/2005 |
| EP | 2957248 A1 | 12/2015 |

(Continued)

OTHER PUBLICATIONS

Forde, Patrick F. et al., "Preclinical evaluation of an endoscopic electroporation system" Electroporation of gastrointestinal cancer . . . Endoscopy, Jul. 2014.

(Continued)

*Primary Examiner* — Sean W Collins
(74) *Attorney, Agent, or Firm* — Knobbe Martens Olson & Bear LLP

(57) ABSTRACT

The invention is within the general field of electroporation. In particular, the invention is within the general field of endoscopic electroporation and relates to a bipolar electrode suitable for endoscopic use, i.e. an electrode assembly that can be inserted in a resectoscope and deployed so as to treat e.g. internal organs tumors, such as bladder, rectum or esophagus.

21 Claims, 14 Drawing Sheets

(52) U.S. Cl.
CPC .......... *A61N 1/0424* (2013.01); *A61N 1/327* (2013.01); *A61B 2018/0016* (2013.01); *A61B 2018/00488* (2013.01); *A61B 2018/005* (2013.01); *A61B 2018/00517* (2013.01); *A61B 2018/00613* (2013.01); *A61B 2018/00982* (2013.01); *A61B 2018/126* (2013.01); *A61B 2018/143* (2013.01); *A61B 2018/1475* (2013.01)

(56) References Cited

U.S. PATENT DOCUMENTS

| | | | |
|---|---|---|---|
| 6,418,341 | B1 | 7/2002 | Hofmann et al. |
| 7,674,249 | B2 | 3/2010 | Ivorra et al. |
| 2002/0151866 | A1 | 10/2002 | Lundkvist et al. |
| 2008/0125775 | A1 | 5/2008 | Morris |
| 2008/0269586 | A1 | 10/2008 | Rubinsky et al. |
| 2010/0298759 | A1* | 11/2010 | Gehl ............ A61N 1/327 604/20 |

FOREIGN PATENT DOCUMENTS

| | | |
|---|---|---|
| WO | WO 03/089046 A1 | 10/2003 |
| WO | WO 2011/075482 A2 | 6/2011 |

OTHER PUBLICATIONS

Gehl, Julie et al., "In vivo electroporation of skeletal muscle: threshold, efficacy and relation to electric field distribution" Biochimica et Biophysica Acta, 1999, pp. 233-240, vol. 1428.

Ørntoft, Mai-Britt Worm, et al., "Endoscopic Electroporation of Tissue—a novel minimally invasive surgical technique", Technology Presentation from Aarhus University, Technology ref. No. 2015-727.

Vásquez, Juan L. et al., "Electroporation enhances mitomycin C cytotoxicity on T24 bladder cancer cell line: A potential improvement of intravesical chemotherapy in bladder cancer" Bioelectrochemistry, 2012, pp. 127-133, vol. 88.

Vásquez, Juan L. "Preclinical studies on electrochemotherapy for bladder cancer", PhD thesis held at the Faculty of Health and Medical Sciences, University of Copenhagen, Feb. 2014.

Vásquez, Juan L. et al., "In Vitro and In Vivo Experiments on Electrochemotherapy for Bladder Cancer" The Journal of Urology, Mar. 2015, pp. 1009-1015, Vo. 193.

Cliniporator—IGEA Clinical Biophysics catalogue—2014—"A simple solution for challenging situations".

International Search Report for PCT/EP2019/080198 dated Feb. 7, 2020.

\* cited by examiner

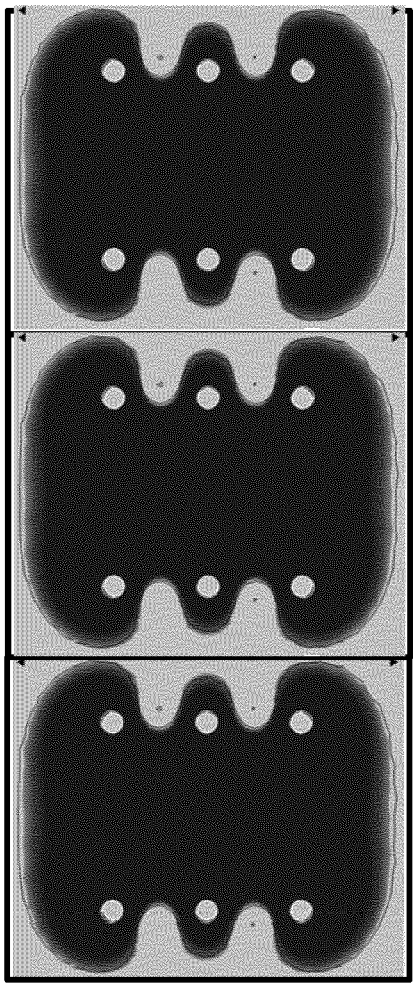
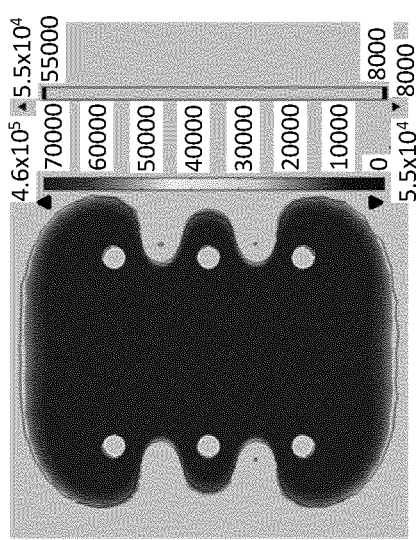
FIG. 5B
FIG. 5A
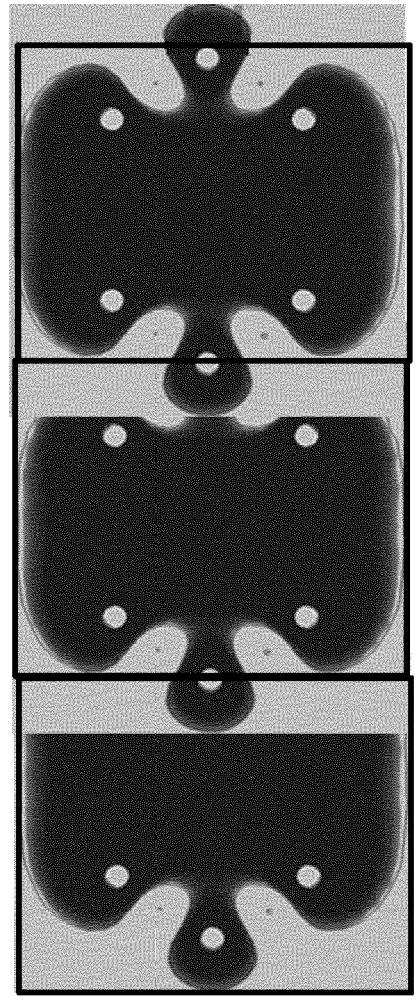
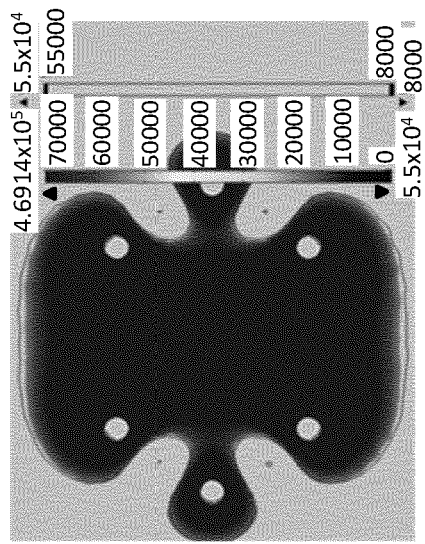
FIG. 6B
FIG. 6A

• Electrode element

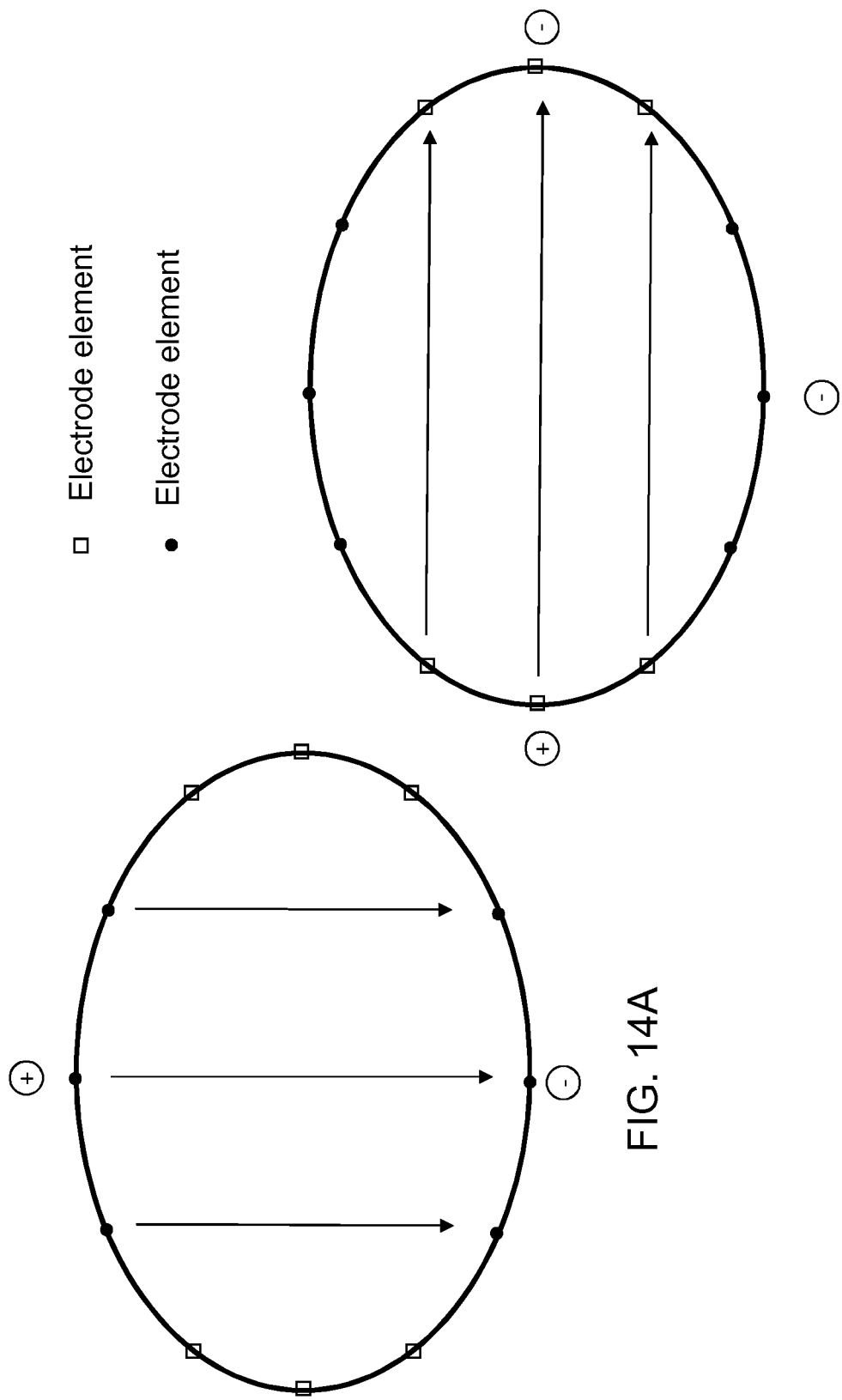

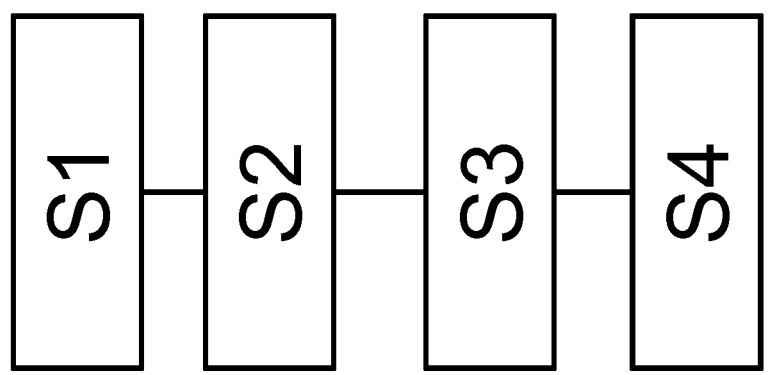

ELECTRODE ASSEMBLY FOR IMPROVED ELECTRIC FIELD DISTRIBUTION

CROSS REFERENCE TO RELATED APPLICATIONS

This application is a U.S. National Phase Application of PCT International Application Number PCT/EP2019/080198, filed on Nov. 5, 2019, designating the United States of America and published in the English language, which is an International Application of and claims the benefit of priority to European Patent Application No. 18204365.3, filed on Nov. 5, 2018. The disclosures of the above-referenced applications are hereby expressly incorporated by reference in their entireties.

FIELD OF THE INVENTION

The present invention relates to an electrode apparatus and electroporation method for creating electric fields that leads to more homogenous field intensities. The present invention also relates to an electrode apparatus for endoscopic use with the aim of performing reversible or irreversible electroporation.

BACKGROUND OF THE INVENTION

Electroporation is widely used for ablation and for drug and gene delivery. Examples include irreversible electroporation, delivery of e.g. chemotherapy (electrochemotherapy), and gene delivery for the treatment of cancer or other diseases. Electroporation may be used for treatment of cancer and other diseases in a number of organs including the head and neck area, lungs, mediastinum, kidneys, liver, colon, rectum, and the genital system as well as the bladder and urinary system. In particular electroporation may be used in the treatment of bladder cancer. Currently, in approximately 40-50% of patients with T1 bladder tumors, i.e. tumors invading the submucosa, conservative treatments fail resulting in increased mortality. Therefore, early radical cystectomy has been suggested as the best option. This surgery implies high morbidity and potential mortality for the patients and has considerable implications on patients' quality of life. Not all patients are fit for this procedure and some are reluctant to have their bladder removed. Furthermore, radiotherapy has limited efficacy in the treatment of these tumors.

Alternative options are very limited. In general, the treatment of bladder tumors is not optimal; the intensive treatment and follow-up in patients receiving conservative treatment, causes substantial inconvenience and morbidity, making cost per patient the highest of all cancers. This has implications for patients with this disease and a heavy burden to society, therefore alternative therapies or improvement of current treatments have been needed for a long time. A possible solution might be improvement of local therapy, which might be a minimally invasive, yet effective, alternative to radical cystectomy in patients with tumors with superficial invasion, i.e. T1, unwilling or unable to undergo major surgery.

Another approach is the trimodality approach, where patients are treated with deep resections of the bladder tumor, chemotherapy and radiotherapy. This modality is very strenuous for patients and is limited to highly selected patients. Hence, an improved device for treatment of bladder tumor or other internal organs tumors would be advantageous, and in particular, a more efficient and reliable for treatment of bladder tumor would be advantageous.

In treating tumors with electroporation, several sequential applications of the electrode is performed to cover the tumor area. Due to inhomogeneities in the electric field, areas with electric fields below the strength needed to deliver the desired treatment, may occur.

Hence a device improving the coverage of the treatment area would be advantageous.

OBJECT OF THE INVENTION

An object of the present invention is to provide an electrode apparatus for treatment.

A further object of the present invention is to provide an electrode apparatus for treatment of bladder tumors or other tumors on the skin or in internal organs, the electrode apparatus being easily, quickly and efficiently operated.

In particular, it may be seen as a further object of the present invention to provide an electrode apparatus and a method to operate it that solves the above mentioned problems of the prior art by providing an electrode arrangements that avoids or reduces the presence of areas with electric fields below the level required for the required effect, i.e. areas having electric field intensities below treatment level, referred to as cold spots thus allowing for a fast and efficient operation of the apparatus.

An object of the present invention is to provide an alternative to the prior art.

SUMMARY OF THE INVENTION

Thus, the above described object and several other objects are intended to be obtained in a first aspect of the invention by providing an electrode apparatus comprising: an electrode assembly comprising a bipolar arrangement of an even number of arrays, such as two or more arrays, wherein each one of the two or more arrays comprises one or more electrode elements; and when in operation, the two or more arrays have opposite polarity; and the one or more electrode elements are arranged or configured to produce an electric field having uniform intensity along an imaginary straight line between the one or more electrode elements having the same polarity.

The electrode apparatus of the invention could be used in treatment of different kinds of tumors.

In some embodiments, the one or more electrode elements of each one of the two or more arrays are one or more curved plate shaped electrode elements, each curved plate shaped electrode elements having an initial, a central and ending part; and the one or more curved plate shaped electrode elements of each one of the two or more arrays are arranged or configured to produce an electric field having uniform intensity along an imaginary straight line between the initial part and the ending part of the one or more curved plate shaped electrode element having the same polarity.

In some embodiments, the electrode elements are plate shaped electrode elements.

In some further embodiments, the electrode elements of each one of the two or more arrays are at least three electrode elements, and wherein the at least three electrode elements of each one of the two or more arrays comprises a first, one or more central and an ending electrode element, and the at least three electrode elements of each one of the two or more arrays are arranged or configured to produce an electric field having uniform intensity along an imaginary straight line between the first and the ending electrode element of said at least three electrode elements having the same polarity.

In some embodiments, the electrode elements are needle shaped electrode elements.

The electrode elements, such as the needle shaped electrode elements are arranged or configured so to minimize the presence of cold spots between the first and ending needle shaped tip, i.e. along the imaginary line connecting the first and the last electrode element. In this way, the electric field produced has an operative cross section allowing for fast treatment of large areas of tissue as the electrode assembly can be rapidly moved between the areas to be treated.

The imaginary line is a geometric straight line that does not physically exist on the electrode apparatus. The imaginary line is a straight line that can be imaginary drawn between the first and the last or ending electrode element connecting and crossing the first and the last electrode element having the same polarity, when in operation.

The wording "crossing" the first and the last electrode element is defined as passing through the center of the first and the last electrode element having the same polarity, when in operation.

In a preferred embodiment, the six needle shaped electrode elements are arranged, configured or adapted so as to provide electric fields that have a homogenous or uniform intensity also along the edges, allowing for efficient and rapid treatment as the electrode assembly can efficiently treat adjacent square or rectangular shaped areas more homogenously. In this way, larger areas may be treated in fast succession.

An electrical field is considered homogenous or uniform when having nearly similar strength/intensity in each point of interest.

The electrical field along the imaginary line between the first and the ending or last electrode element has thus a similar value.

Similar value may be defined as a value of the electrical field being the same or being within 10% to 50% higher or lower than the same value.

For example, similar value may be a value within 20% to 50% higher or lower than the same value, such as a value within 30% to 50% higher or lower than the same value.

The similar value may be a value of the electrical field being within 40% to 50% higher or lower than the same value.

The bipolar arrangement of the invention, i.e. the arrangement in which one or more center electrode elements are off-set, avoids the presence of a "butterfly shaped" electric field intensity region between adjacent electrode elements having the same polarity.

The drawback of the presence of a "butterfly shaped" electric field intensity region is that during operation, in order to ensure exhaustive treatment of all interested areas substantial overlapping of the treated areas may be required leading to potential tissue damage.

By producing an electric field having uniform intensity along the line drawn between the first and the ending electrode elements and thus producing a more square shaped electrical field intensity region there is no need of large overlapping during treatment, which would lead to tissue damage during operation. This solution leads to a faster and more efficient application of the electroporation treatments and improves the efficiency of the electroporation treatments, with potentially minimal tissue damage.

In some embodiments, the electrode elements are needle shaped electrode elements and have needle shaped tips.

In some other embodiments, the electrode elements are needle shaped electrode elements having round shaped tips.

The bipolar arrangement of an even number of arrays may be of at least two arrays or of two or more arrays, i.e. a series of electrode elements having, for example needle shaped tips.

The bipolar arrangement has at least one array of at least three needle shaped electrode elements having the same polarity and at least one array of at least three needle shaped electrode elements having the opposite polarity.

When in operation, the opposing polarities create an electric field that is characterized by uniform intensity along an imaginary straight line between the first and the ending electrode elements of each array.

The specific way in which the electrode elements are arranged or configured produces an electric field intensity region that have a square or rectangular shape cross section avoiding cold spots along the imaginary line connecting the first and the last electrode elements, thus having an uniform intensity, i.e. having an electric field having similar value, along the imaginary line connecting the first and the last electrode elements.

In other words, this specific configuration produces an electric field region having a square or rectangular shape cross section avoiding cold spots along the imaginary line, when in operation.

This is achieved by having the one or more central electrode elements offset of the imaginary straight line between the first and the ending electrode element.

This allows for fast treatment of large areas of tissue as the electrode assembly can be rapidly moved over the treatment area.

According to the invention, at least three electrode elements have a positive polarity and at least three electrode elements have a negative polarity.

Thus, in one aspect the invention relates to an electrode apparatus comprising: an electrode assembly comprising a bipolar arrangement of an even number of arrays, such as two or more arrays, wherein each one of the two or more arrays comprises one or more electrode elements; and wherein the two or more arrays have opposite polarity, when in operation; and wherein the electrode elements of each one of the two or more arrays are at least three electrode elements, and wherein the at least three electrode elements of each one of the two or more arrays comprises a first, one or more central and an ending electrode element, and the at least three electrode elements of each one of the two or more arrays are configured to produce an electric field having uniform intensity along an imaginary straight line between the first and the ending electrode element of the at least three electrode elements having the same polarity, the imaginary line connecting and crossing the first and the ending electrode element having the same polarity; and the one or more electrode elements are configured to produce an electric field having uniform intensity along the imaginary straight line, and wherein the one or more central electrode element are offset of the imaginary straight line, thereby producing, an electric field region having a square or rectangular shape cross section avoiding cold spots along the imaginary line, when in operation.

The invention is within the general field of electroporation, such as endoscopic electroporation and in particular relates to a bipolar electrode device suitable for endoscopic use, i.e. an electrode device that can be inserted in a resectoscope and deployed so as to treat e.g. internal organs tumors, such as bladder, colon-rectal or esophageal cancer.

The electrode apparatus, according to the invention, is characterized by the presence of at least six electrode elements of opposite polarity (three positive and three negative). The position of the electrode elements, i.e. characterized by one or more central electrode elements not in line with the other electrode elements produces a square/rectangular shaped electrical field intensity region. In this way, by moving the electrode apparatus systematically throughout the area to be treated, a more homogenous coverage of the tissue to be treated is achieved reducing the presence of "cold" spots. This effect cannot be achieved by the presence of only two electrode elements as a gap between the electrode elements in the electric field will appear, i.e. a butterfly shaped electrical field will be produced not allowing for homogenous coverage of the area to be treated. Further advantages of the invention include: visual access to the area to be treated and thus the possibility of immediate treatment after ablation; use in space restricted conditions (e.g. within an endoscope) due to potential optimization of the geometry and position of the electrode elements and intensity of the electrical field.

The electrode elements may be in the form of needle shaped electrode elements that may be fixed in a determined position and may have a sharp tip so as to be able to penetrate the area to be treated. However, rounded tips may be also envisaged.

In some embodiments neighboring electrode elements of the same array may be equidistant from each other.

In some other embodiments, the distance between the electrode elements may be different.

Shape and size of the electrode elements may vary within the same electrode assembly.

Shape and size of the electrode elements may vary within the bipolar arrangement.

A further advantage of the electrode apparatus of the invention is that, since tumor resection, e.g. in the bladder, is normally performed with a resectoscope, the electrode assembly of the invention could be replaced with different ex-changeable instruments such as a loop electrode for resection or roller ball for coagulation.

A further advantage is that the positioning of the electrode elements renders the electrode assembly and the area where it is going to be applied always visible. In that by introducing the electroporation electrode assembly in a resectoscope, electroporation can be easily added to potential treatment of the bladder.

For example, following tumor resection, the loop electrode used for resection can be easily changed and the electrode assembly of the invention can be introduced to treat the resected area in order to kill remaining cancer cells, which are potentially responsible for recurrence and progression.

In some other cases, the electrode assembly of the invention can also be applied directly to smaller bladder tumors thus avoiding the need of resection. The electroporation procedure is very fast, delivering pulses e.g. in the microsecond range. In a short period of time different areas of the bladder can be treated. Importantly the location of the electrode elements allows for a homogenous treatment while moving the electrode assembly along the area to be treated as the field produced has a rectangular shape, thus ensuring coverage of the area of interest.

In a preferred embodiment, the electrode elements in the form of needles penetrate the tissues to be treated. In some embodiments, the needles may only be in surface contact with the tissue to be treated.

For example, the length of the electrode elements are shaped as needles and allows treatment of the full thickness of the bladder wall, thus enabling treatment of cancer cells deeply hidden in the bladder wall.

The electrode assembly of the invention allows for improving the success of electrochemotherapy or other electroporation based treatments as single treatments, such that following tumor resection, electroporation treatment of surrounding cells and eventual deeper cells, provides an effective and minimally invasive alternative treatment to surgical removal of the whole organ, for example the bladder. Taking in consideration the anti-vascular effect of electrochemotherapy, the electrode assembly of the invention can also be used for the palliative treatment of bleeding tumors, as a single session, where the alternative is palliative radiotherapy that requires several sessions.

The electrode assembly of the invention allows for the specific use of electroporation in the bladder.

The arrangement of electrode elements in a circular array has also the benefit of allowing for better visual approach to the tissue to be treated. Indeed no visual hindrance is present as the needles are located around the optical axis, and insertion into tissue can be directly visualized.

The electrode apparatus may also comprise a pulse generator and/or a resectoscope. The electrode assembly is to be adaptable to existing endoscopes that are used for resection of bladder tumors.

In general, electroporation is a technique where the cell membrane integrity is briefly disrupted by an electrical field, and afterwards the cell membrane is more permeable for substances for a given period of time.

Reversible electroporation leaves the cell viable and capable of re-establishing the membrane integrity, whereas irreversible electroporation disrupts the cell membrane to such a degree, that the cell undergoes cell death.

Electroporation of tissues can have several purposes: Reversible electroporation can facilitate cellular internalization of molecules, e.g. drugs such as chemotherapy, gene medicines e.g. in the form of DNA or RNA, otherwise too large to penetration of the cell wall.

Irreversible electroporation can facilitate cell death and as such can be an alternative to e.g. thermal ablation.

Depending on the therapy, the electric field intensity applied may need to be quite different. For electrochemotherapy 550 V/cm is the optimal intensity, while for gene electro-transfer the intensity is in the area of 80V/cm.

The idea of the invention is to facilitate electroporation through an endoscope to target tissue, such as mucosa, of a luminal organ, such as the intestine or the bladder, through a suitable device and electrode assembly.

In some embodiments, the one or more central electrode element(s) are offset of the imaginary straight line between the first and the ending electrode element.

Offset is defined as placed out of line, i.e. not along the imaginary straight line between the first and the ending electrode elements.

The electrode elements are arranged or configured so that the one or more central electrode elements are never on the imaginary line connecting the first electrode element and the ending electrode element of the group of three or more electrode elements having the same polarity.

In some embodiments, the imaginary straight line is an imaginary straight line between a tip of the first and a tip of the ending electrode element of the at least three electrode elements having the same polarity.

In some embodiments, the electrode assembly is a retractable electrode assembly.

In some embodiments, the electrode apparatus further comprises an endoscopic sheath; and wherein the retractable electrode assembly is suitable for endoscopic use.

An endoscopic sheath may also be referred to as endoscope.

The retractable electrode may thus be suitable for being introduced into an endoscope or endoscopic sheath.

In some embodiments, the first, one or more central and ending electrode elements are a number of first, one or more central and ending electrode elements.

In that, bipolar arrangements may comprise arrays having more than one first, central and ending electrode elements. For example, the bipolar arrangement may comprise arrays having two or more first, two or more central and two or more ending electrode elements. In some embodiments, the bipolar arrangement may comprise arrays having one first, two or more central and one ending electrode element.

In some embodiments, the one or more central electrode elements are offset by or within 0.75 and 1.75 mm, such as within 1 and 1.5 mm, such as 1.25 mm, from the imaginary straight line between the first electrode element and the ending electrode element of the at least three electrode elements having the same polarity.

Optimizations in electrode element positioning shows optimal values of coverage when the offset is within 0.75 and 1.75 mm from the imaginary straight line between the first electrode element and the ending electrode element.

In general, the optimal offset will depend on the size and the number of electrode elements as well as on the distance between the opposed electrode elements. Size, shape and thickness of the electrode elements may also have an influence in determining the optimal offset value.

It may therefore be assumed that scalability of the electrode apparatus and the electrode elements will influence the optimal offset values.

In some further embodiments, the bipolar arrangement is an arrangement, such as a polygonal arrangement, wherein the two or more arrays surround the optical axis of the endoscopic sheath.

This configuration does not hinder the field of view, since the two or more arrays surround the optical axis of the endoscopic sheath. This ensures clear visual access to the area to be treated and thus the possibility of immediate treatment after resection.

Polygonal arrangement may be, e.g. triangular, square, rectangular, pentagonal or hexagonal.

In some embodiments, the at least three electrode elements of each one of the two or more arrays are arranged along a perimeter of the bipolar arrangement.

In some further embodiments, the bipolar arrangement is a circular arrangement wherein the two or more arrays surround the optical axis of the endoscopic sheath.

The bipolar arrangement is a circular arrangement wherein the at least three electrode elements of each one of the two or more arrays are circularly arranged around the optical axis of the endoscopic sheath.

The one or more central electrode element of each array of the at least three electrode elements having same polarity are located offset an imaginary chord between the first and the ending electrode elements of the at least three electrode elements having the same polarity.

The at least three electrode elements of each one of the two or more arrays are arranged along a circumference of the circular arrangement.

The first, one or more central and ending electrode element of each one of the two or more arrays are arranged on opposite locations of the bipolar arrangement.

In some embodiments, the at least three electrode elements have a positive polarity and the at least three electrode elements have a negative polarity and at least three elements having a positive polarity are arranged on the perimeter of a first half of the circular arrangement and the at least three electrode elements having a negative polarity are arranged on the perimeter of a second opposite half of the circular arrangement.

In some other embodiments the even number of arrays is four and a first bipolar arrangement of two arrays having positive polarity and negative polarity and a second bipolar arrangement of two arrays having positive polarity and negative polarity are located along the circumference of one or more separated concentric rings.

In some embodiments, the bipolar arrangement comprises two concentric ring arrangements wherein the two arrays having positive polarity are located on opposite sides of two arrays having negative polarity.

This arrangement is more versatile than other arrangements as the electric field applied may be easily changed by applying a voltage to either the inner or the outer ring.

The at least six electrode elements may have tips having sharp outer surface geometry.

A sharp or pointed tip allows for penetration of the area to be treated.

In some embodiments, the at least six electrode elements have tips having a blunt or rounded outer surface geometry or rounded tip.

A blunt or rounded tip is a smooth non-cutting shape in order to limit the depth of the treatment.

In this case, the electrode assembly may operate with the electrode elements in contact to the area to be treated.

The electrode assembly may have a cross section in the range between 40 and 1 mm.

The retractable electrode assembly may have a cross section of 40 mm or less, preferably 30 mm or less, more preferably 20 mm or less.

The cross section may also be circular thus with an outer diameter of 40 mm or less, preferably 30 mm or less, more preferably 20 mm or less, such as 10 mm or less, for example 5 mm or less.

Cross section may also have other shapes, such as oval or polygonal.

The upper range of the cross section may be determined by the use, i.e. a limitation on the size of the cross section may be due to the use within an endoscopic sheath, being the cross section according to the endoscope.

The electrode apparatus may further comprise an electric pulse generator.

The electrode assembly may further comprise a source of electric stimuli so as to make the electrode assembly suitable for different uses.

In some embodiments, the electric pulse generator supplies single electrical pulses or sequence of electrical pulses according to electroporation protocols for drug and gene delivery.

In some other embodiments, the electric pulse generator supplies single electrical pulses or sequence of electrical pulses according to irreversible electroporation protocols.

In some further embodiments, the endoscopic sheath is a resectoscope.

In this way, electroporation treatment may occur immediately after resection of the tumor, e.g. in the treatment of tumors in the bladder or other organs.

The electroporation assembly of the invention may be applied in different conditions and for different purposes. In a palliative setting the electrode assembly may be used for bleeding tumors as electrochemotherapy has profound effect on tumor vasculature, causing immediate cessation of bleeding. Furthermore, electrochemotherapy could be tested on patients with muscle invasive tumors, in the neoadjuvant setting.

The device of the invention may be applied to treatment of bladder tumors and different type of tumors of internal organs.

The electrode assembly of the invention may primarily provide benefits to the treatment when used in the bladder. However, devices with electrode assemblies with electrode elements arrayed as described in this invention may be used for the treatment of tumors present in other internal organs, in particular where the access to the organ is performed endoscopically, even by a flexible endoscope. For example these organs may be: esophagus, rhinopharynx, sinuses, trachea, endometrium, cervix cancer, larynx, and pharynx. Furthermore, in the veterinary setting, where one-time treatment may be necessary, the device and electrode assembly of the invention may be used providing several advantages.

In a second aspect, the invention relates to an electroporation method for creating one or more electrical fields to generate an electroporation and/or electrophoretic effect in a target tissue in a luminal organ, the method comprising: providing an electrode apparatus according to the first aspect of the invention; inserting the electrode assembly through tissues of a body via insertion of a cannula or sheath or into a luminal organ by endoscope and bring into a vicinity of a target region to be treated, while the retractable electrode assembly is in a retracted position;
    extending said retractable electrode assembly to an extended position to at least partially surrounding tissue in a target region to be treated; and
    transmitting from said retractable electrode assembly one or more electric pulses of specific amplitudes and durations to create one or more electric fields in said target region.

In some embodiments, the electroporation method according to the second aspect of the invention, further comprises a step of administering a dose of therapeutic molecules through the endoscopic sheath, while or before applying through the electrode assembly the one or more pulses.

The first, second and other aspect and embodiments of the present invention may each be combined with any of the other aspects or embodiments. These and other aspects of the invention will be apparent from and elucidated with reference to the embodiments described hereinafter.

BRIEF DESCRIPTION OF THE FIGURES

The electrode assembly and electroporation method for creating electric fields employing an electrode assembly according to the invention will now be described in more detail with regard to the accompanying figures. The figures show one way of implementing the present invention and are not to be construed as being limiting to other possible embodiments falling within the scope of the attached claim set.

FIG. 5A shows the electrode assembly with electrode elements in a linear layout.

FIG. 5B shows the electrical field coverage created by moving the electrode apparatus during the electroporation procedure using linear electrode elements arrays.

FIG. 6A shows the effect of off-setting the central electrode in terms of treatment field coverage.

FIG. 6B shows the electrical field coverage created by moving the electrode apparatus during the electroporation procedure using offset electrode elements arrays.

FIGS. 14A and 14B show how perpendicular assemblies may be used in the electrode array set-up.

FIG. 15 is a flow-chart of a method according to one aspect of the invention.

DETAILED DESCRIPTION OF AN EMBODIMENT

This new electrode apparatus with a novel array of electrode elements provides a better electric field distribution.

The electrode assembly may be applied for any electroporation based treatment in the skin, or cutaneous and subcutaneous tumors, as well as for treatments in internal organs.

These treatments include delivery of drugs or genes by reversible electroporation, as well as irreversible electroporation.

The electrode apparatus of the invention can also be used for electroporation-based treatments of diseases in internal organs. This electrode assembly may be used endoscopically through a sheath, e.g. in the bladder. The electrode may also be adapted to a resectoscope, which is an endoscopic device used for the resection of bladder tumors. The electrode assembly is designed to have needle-shaped electrode elements that penetrate in the area that is to be treated, in order to apply an electric field that is capable to produce electroporation, i.e. permeabilization of the cell membrane of the target cells for the introduction of molecules that will induce the desired effect on the tissue. Electroporation-based treatments: electrochemotherapy, irreversible electroporation, electrogene-transfer, i.e. gene therapy, calcium electroporation, have shown promising results in the treatment of cancers of different histologies.

In the case of bladder cancer, in vitro and in vivo studies have shown that electrochemotherapy using mitomycin C and cisplatin is more effective than chemotherapy alone for experimental bladder cancer tumors and on the base of those findings, the inventors designed the electrode assembly according to the invention.

Figure 1:
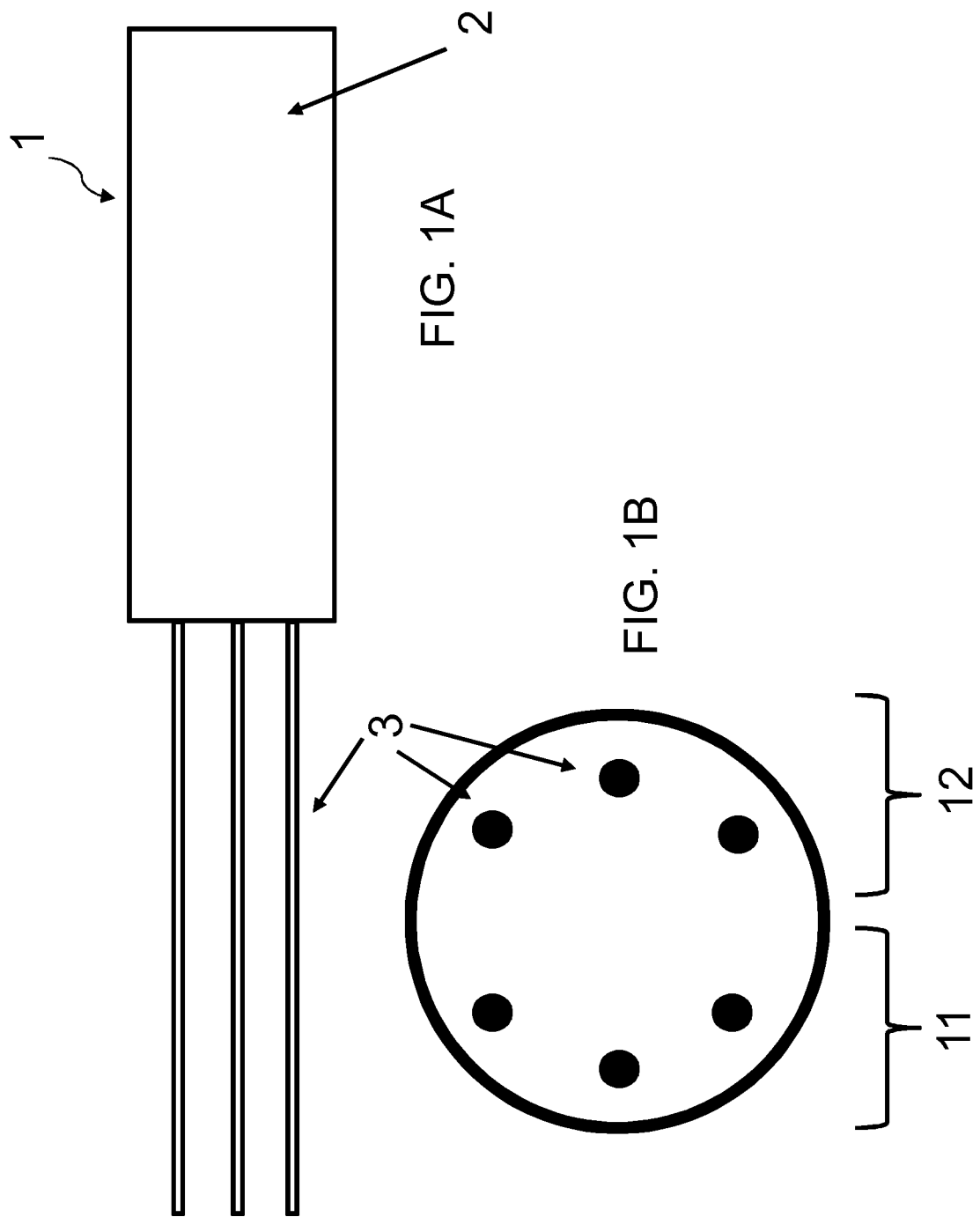
FIG. 1 shows a schematic representation of a side (1A) and a front (1B) view of an electrode assembly according to some embodiments of the invention.

FIG. 1 shows a schematic representation of a lateral view (1A) and a frontal view (1B) view of an electrode assembly (1) having a main body (2) and six needle-shaped electrode elements (3) extending from the main body (2).

The six needle-shaped electrode elements are arranged into two arrays (11) and (12), having each three electrode elements, and having opposite polarity while in operation.

Figure 2:
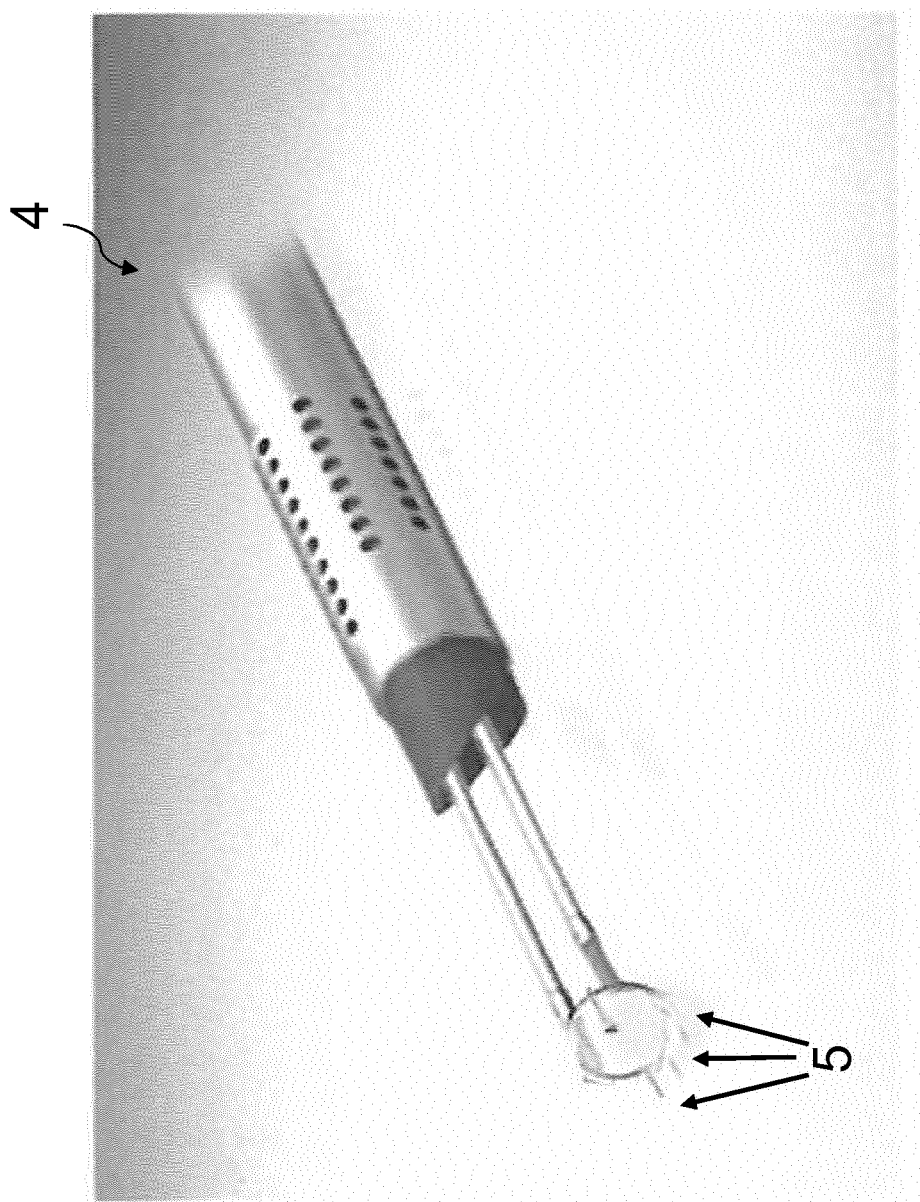
FIG. 2 shows an example of a 3D view of an electrode assembly according to some embodiments of the invention.

FIG. 2 shows an example of a 3D view of an electrode assembly according to some embodiments of the invention in which the electrode assembly comprises a device (4) having 6 needle-shaped electrode elements (5) with a length of 5 mm and an outer diameter of 0.4 mm arranged onto a circularly shaped platform. Each half of the circularly shaped platform is isolated from the other and electrically chargeable. These needle-shaped electrode elements are arranged in such a way that the holding platform with needle-shaped electrode elements may be fitted in an endoscope, allowing visualization of the bladder through standard optical endoscopic equipment. The dimension of the equipment allows for leads to be drawn through such an endoscope, thus making endoscopic electroporation possible under visual guidance and within the size constraints of an endoscopic device, as for example used in the bladder. The dimensions allow for both reversible and irreversible electroporation.

Figure 3:
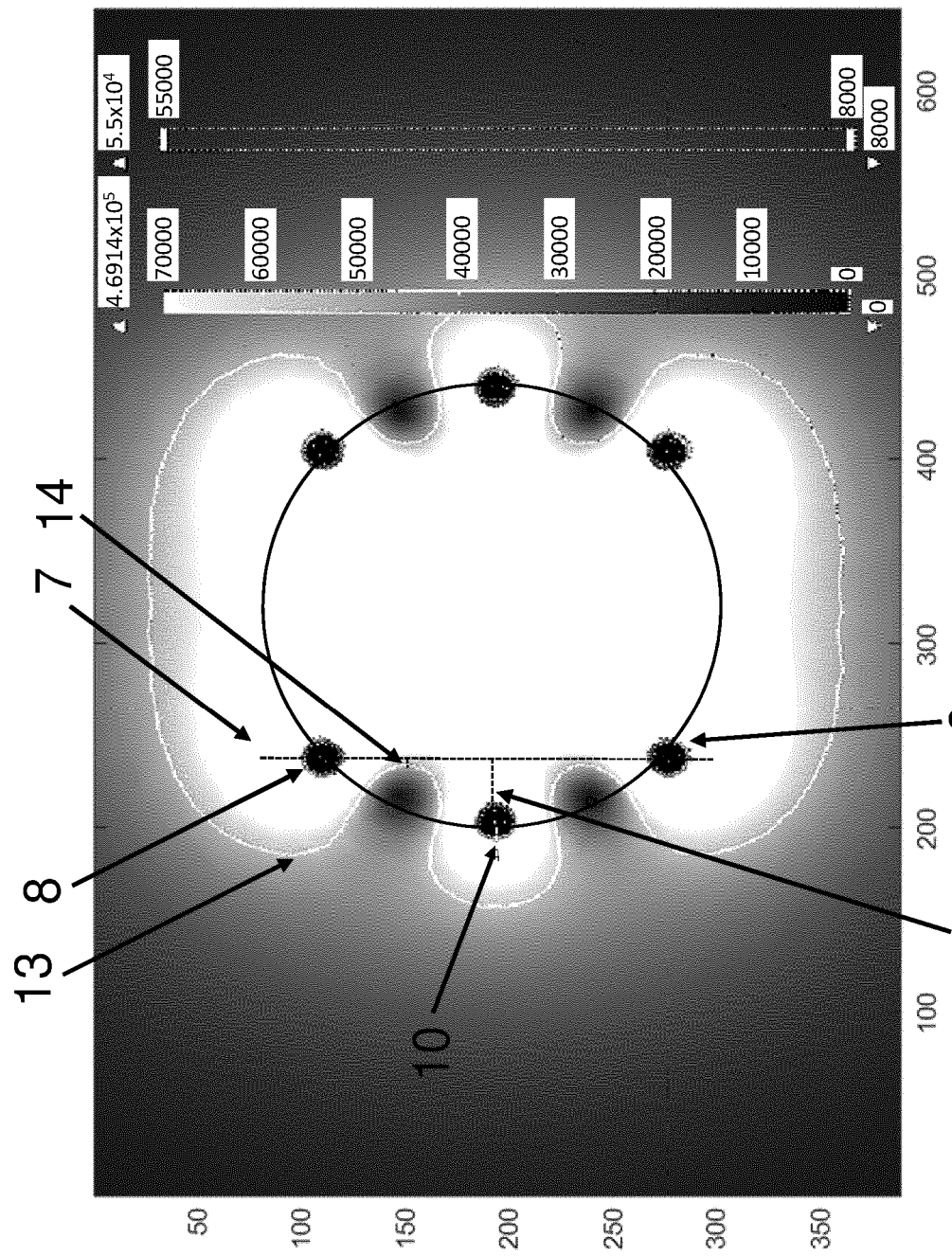
FIG. 3 cross section of the electrical field intensity distribution at half electrode assembly length according to some embodiments of the invention.

FIG. 3 shows calculated electric field intensity distribution in a top view for an electrode assembly according to some embodiments of the invention.

FIG. 3 shows intensities at half electrode element length, i.e. at 2.5 mm as a top view, i.e. when the electrodes are perpendicular to the paper.

The electrode offset distance (EOD) (6) is defined as the distance from in-line position i.e. the linear layout. EOD is therefore the distance of the central electrode element (10) from an imaginary straight line (7) between the first needle-shaped electrode element (8) and the ending needle-shaped electrode (9) of the at least three electrode elements having the same polarity.

In this example of an embodiment of the invention the EOD refers to the distance of the central electrode (10) from the imaginary straight line (7).

As mentioned above, the optimal offset will depend on the size and the number of electrode elements as well as on the distance between the opposed electrode elements. Size, shape and thickness of the electrode elements may also have an influence in determining the optimal offset value. It may therefore be assumed that scalability of the electrode apparatus and the electrode elements will influence the optimal offset values.

This electrode geometry is referred to as 'reference' in the following.

Figure 4:
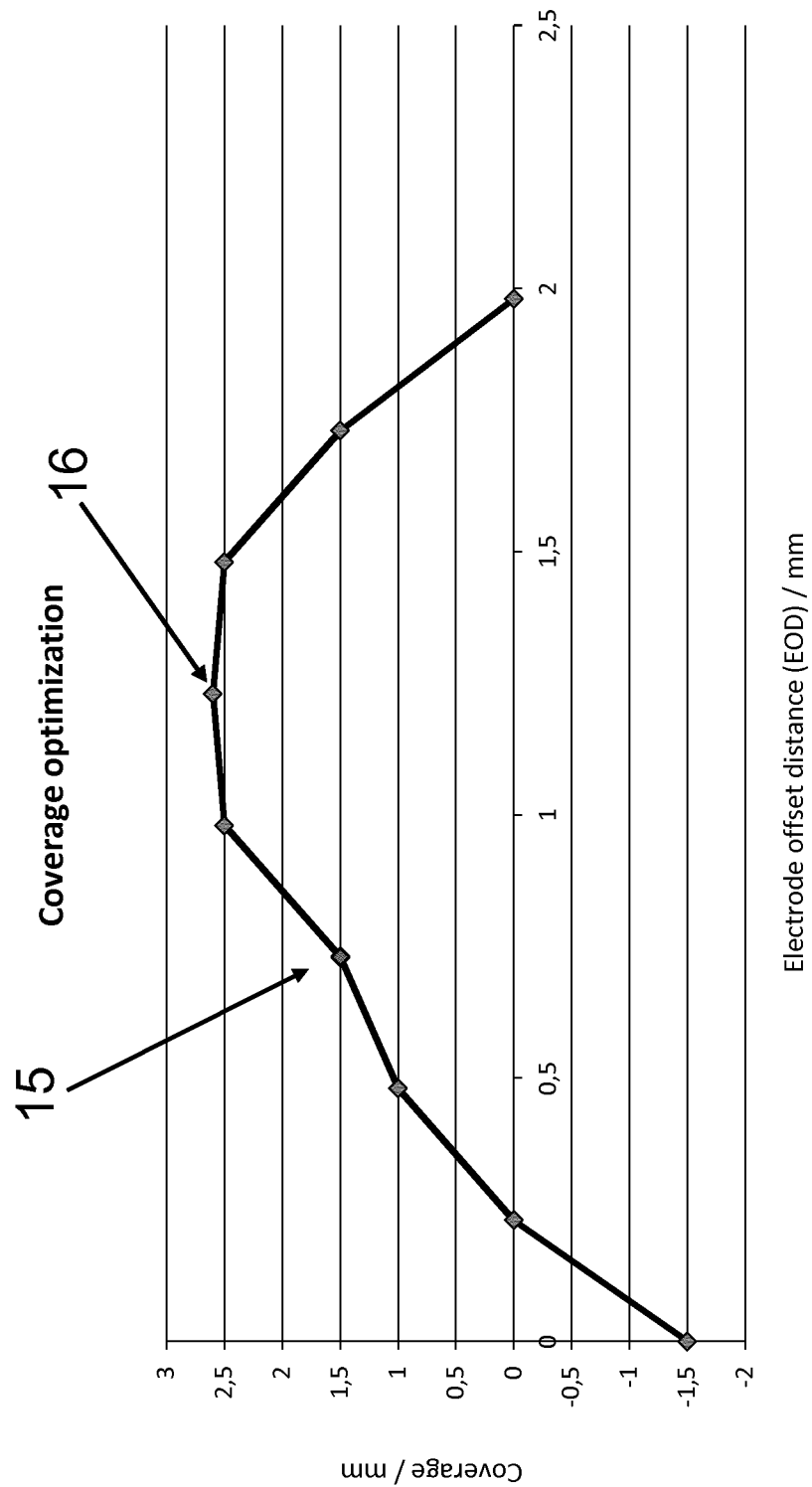
FIG. 4 shows a coverage optimization study showing the optimal Electrode Offset Distance (EOD) for having optimal coverage.

FIG. 4 shows a coverage optimization study showing the optimal EOD for having optimal coverage.

Coverage is defined as the shortest distance from the imaginary straight line (7) to the 550 V/cm iso-field line, which is the minimum field intensity required for sufficient treatment. Coverage is positive in the outwards direction with respect to the imaginary straight line (7).

In FIG. 4 the coverage (14) is indicated as the shortest distance between the imaginary straight line (7) and the 550 V/cm iso-line (13).

From the study it appears clear that optimal coverage (16) is achieved with an electrode offset distance between 1 and 1.5 mm, i.e. with an optimal coverage at EOD=1.25 mm.

This layout is referred to as 'optimal' in the following.

EOD=0 corresponds to the linear layout, and has negative iso-line distance.

The optimal coverage as mentioned above is at EOD=1.25 mm as shown in FIG. 4.

The reference electrode geometry shown in FIG. 3 correspond to a coverage of 1.5 and is shown by point 15.

The difference between the linear and the optimal layout are shown in FIG. 5A and FIG. 6A respectively.

FIGS. 5B and 6B show positioning of adjacent treatment fields with the above mentioned linear geometry (5A) and off-set central electrode element geometry (6A).

In FIGS. 5B and 6B, squares are inserted showing the planned treatment area. When performing treatments using electroporation the electrode apparatus will be moved so that the entire area is sequentially treated. By inserting into the previous electrode position, adequate coverage can be attempted. In FIG. 5B (linear electrode) it can be seen that areas between the electrode elements of same polarity are not sufficiently covered, whereas in FIG. 6B the coverage defects within the rectangular shape are not present, as a result of off-setting the central electrode element.

In conclusion, FIG. 5B shows that, during electroporation procedure, the movement of the electrode apparatus having linear arrays on the treated area will either lead to areas with low and thus inefficient electrical field or to substantial overlap and thus overexposure causing tissue damage.

On the contrary, the solution of the invention, as shown in FIG. 6B, avoids the overlap issues and provides uniform electrical field to the treated area through the all electroporation procedure.

Figure 7:
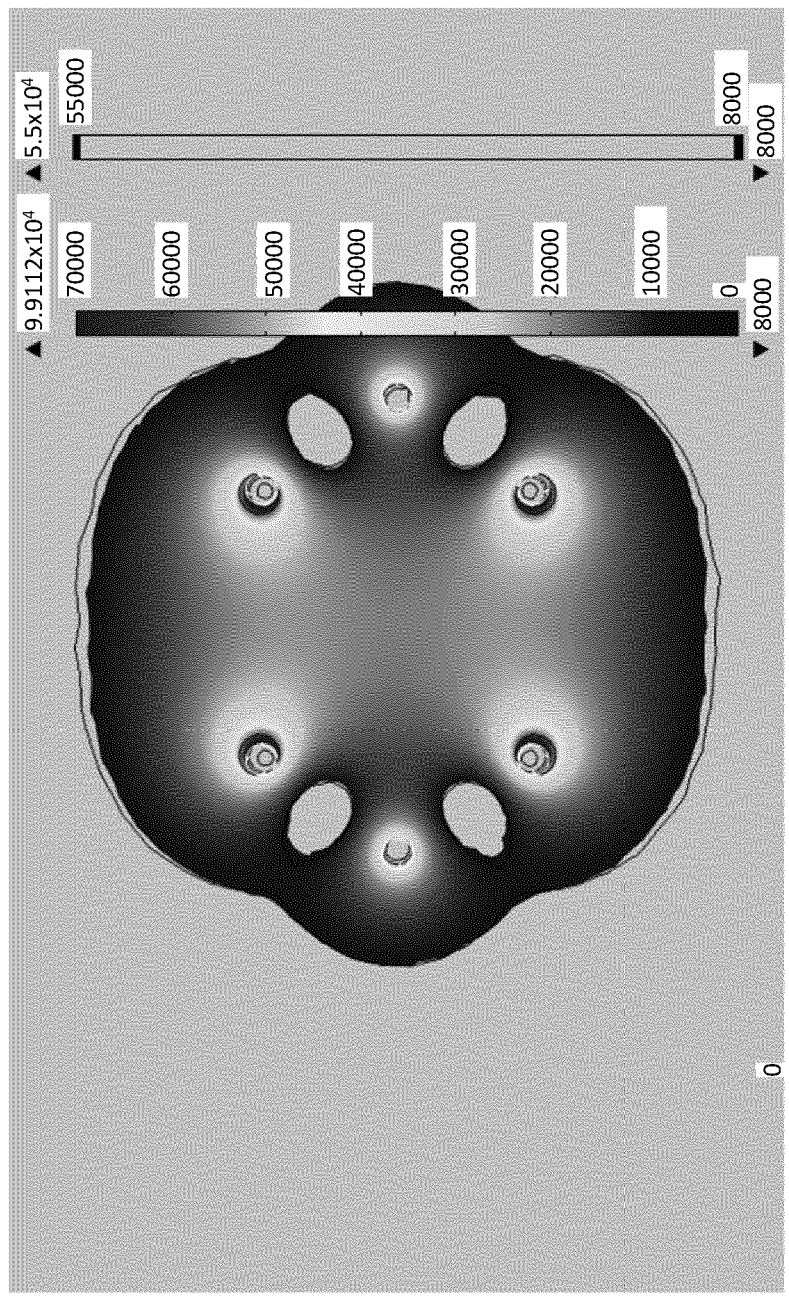
FIG. 7 shows electrical field calculation for the optimal layout at 80 V/cm coverage using an applied voltage of 100 V.

FIG. 7 shows electrical field calculation for the optimal layout at 80 V/cm coverage at 100 V between electrode elements of each array In some embodiments, the electrode assembly may comprise further electrodes elements.

Figure 8:
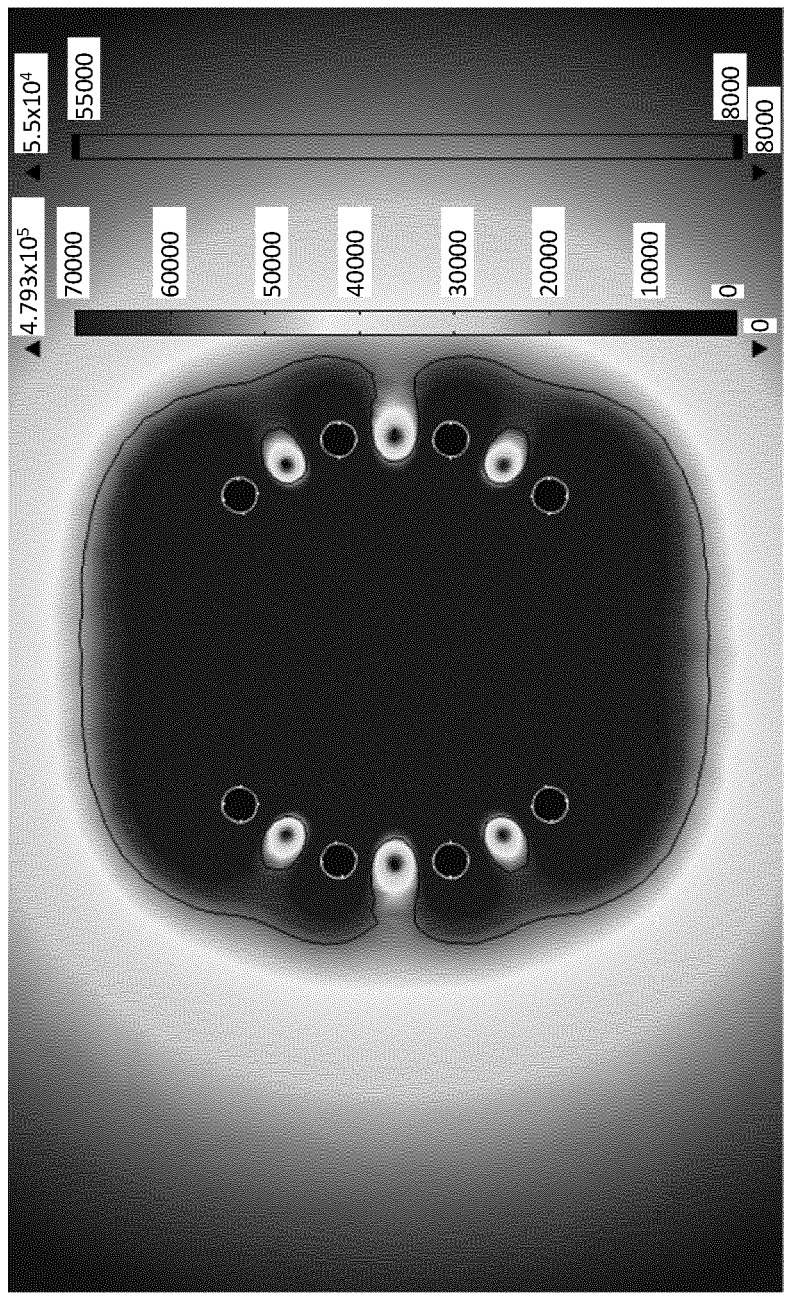
FIG. 8 shows electrical field calculation for an eight needle version of the electrode assembly in the reference layout.

FIG. 8 shows electrical field calculation for an assembly of eight electrode elements of the electrode assembly in the reference layout.

Figure 9:
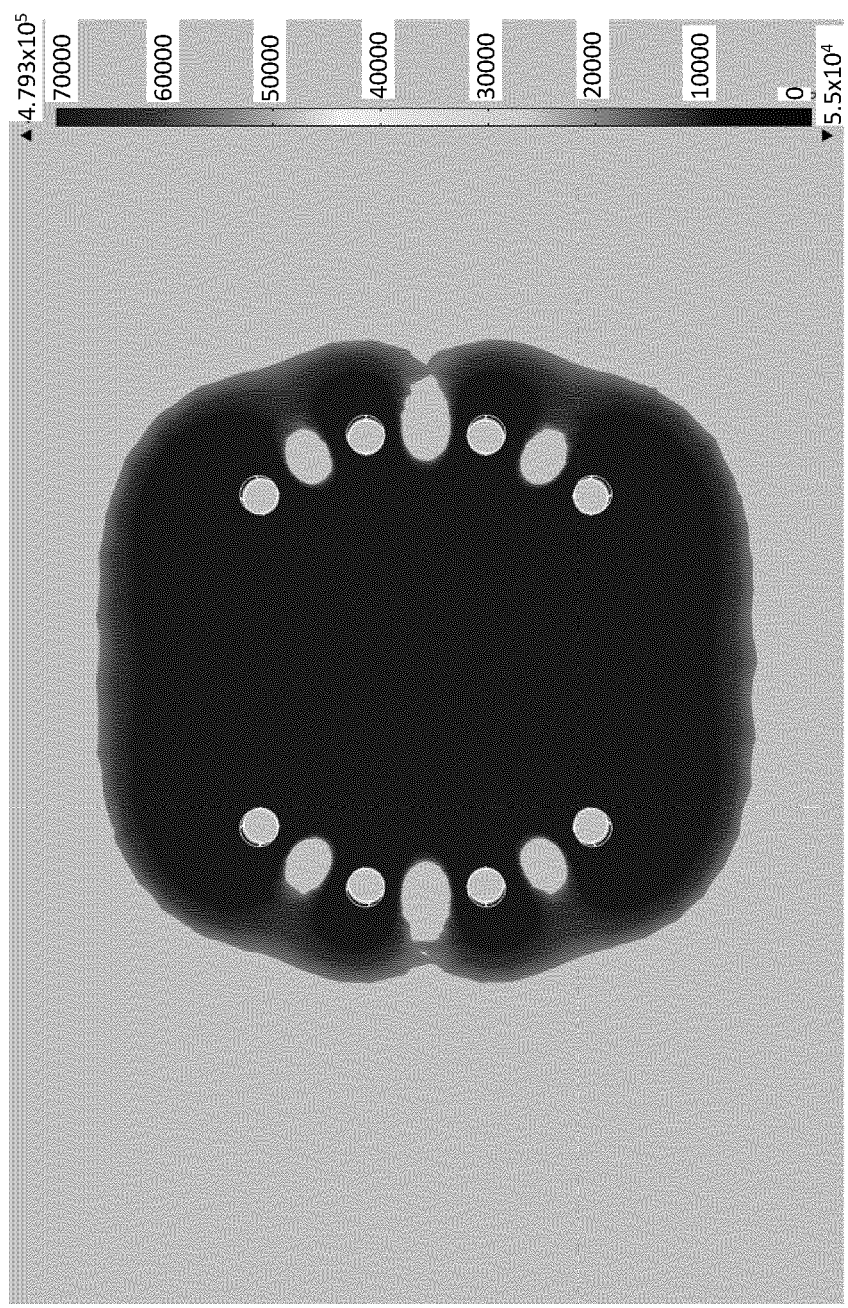
FIG. 9 and FIG. 10 shows electrical field calculations aiming at studying the effect of variable needle radius and different needle thickness.
Figure 10:
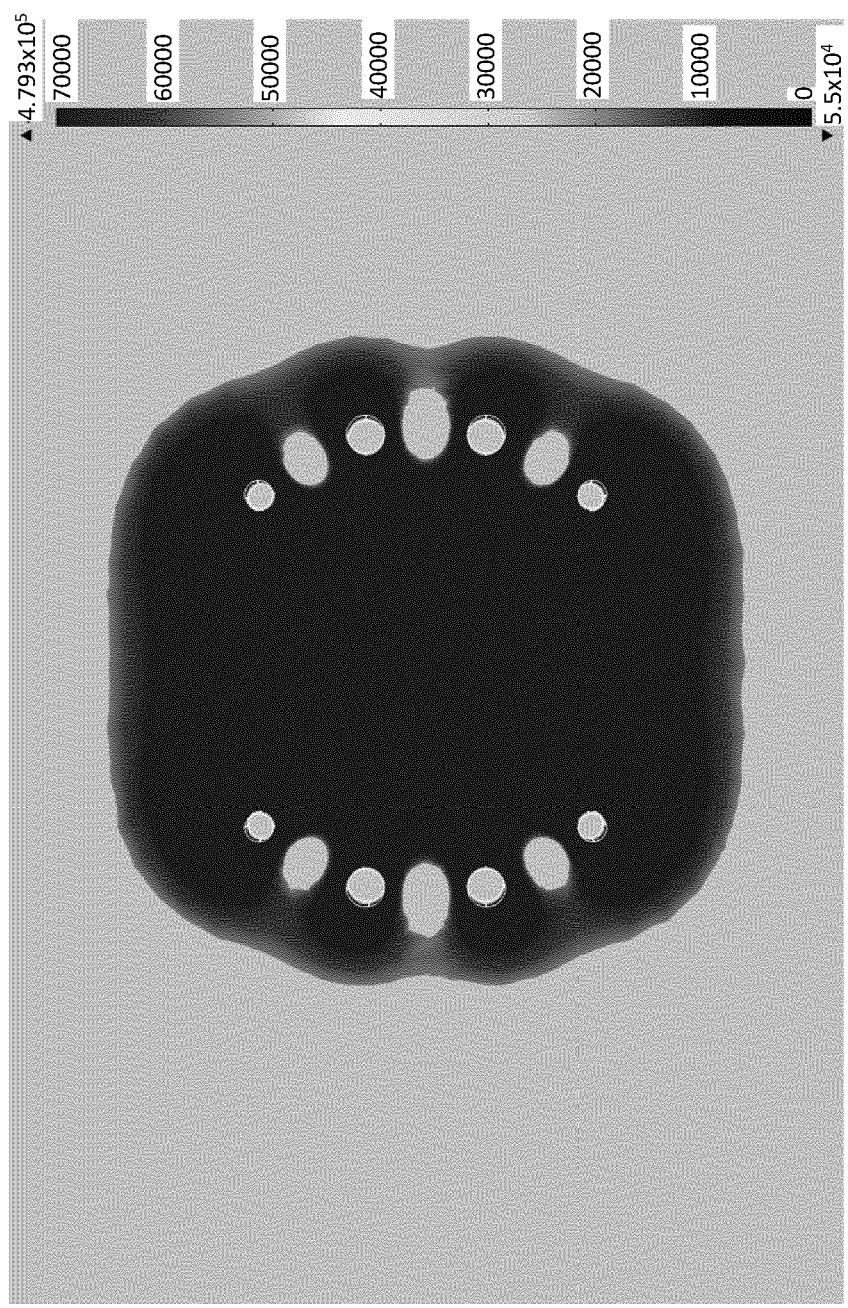

FIG. 9 and FIG. 10 show electrical field calculations aiming at studying the effect of variable electrode elements radius and thickness.

FIG. 9 shows an eight electrode element configuration with electrode elements of equal thickness, i.e. 0.2 mm radius.

FIG. 10 shows an assembly having thinner end electrode elements, such as 0.15 mm in radius, while the central electrodes has a thickness of 0.20 mm radius. As the average distance to the opposing electrode element is smaller, the reduced radius of the of the first and ending electrode elements, does not affect coverage.

The average distance of the lateral electrode elements to the opposing electrode elements is less than that of the central electrodes. This renders variable radius feasible, i.e. it can be observed that there is no reduction of coverage having lateral electrode elements, i.e. the first and the ending electrodes, having reduced radius.

Figure 11:
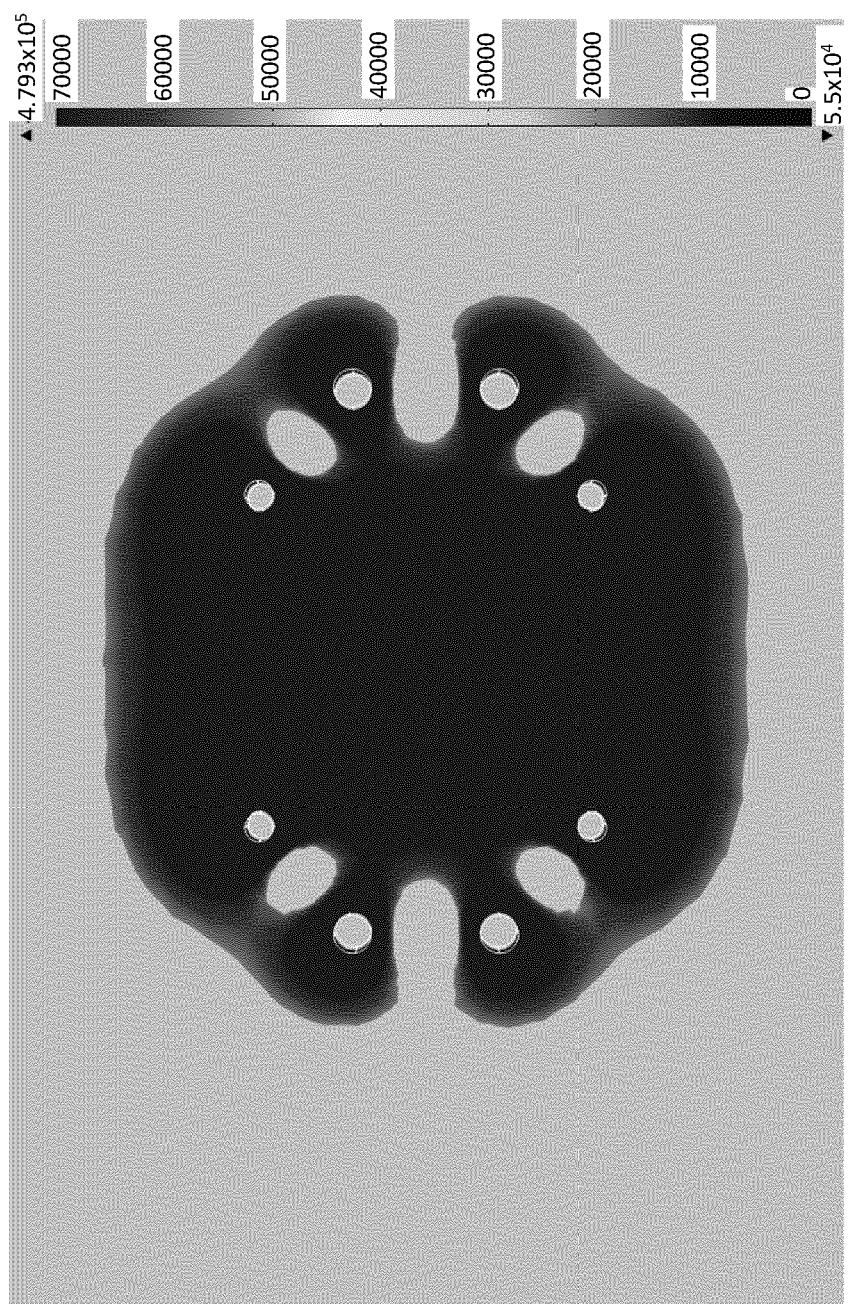
FIG. 11 shows electrical field calculation for an eight-needle version of the electrode assembly in which all electrode elements are equidistant.

FIG. 11 shows electrical field calculation for an 8 electrode elements version of the electrode assembly in which all electrode elements have equal thickness (0.2 mm radius).

Figure 12:
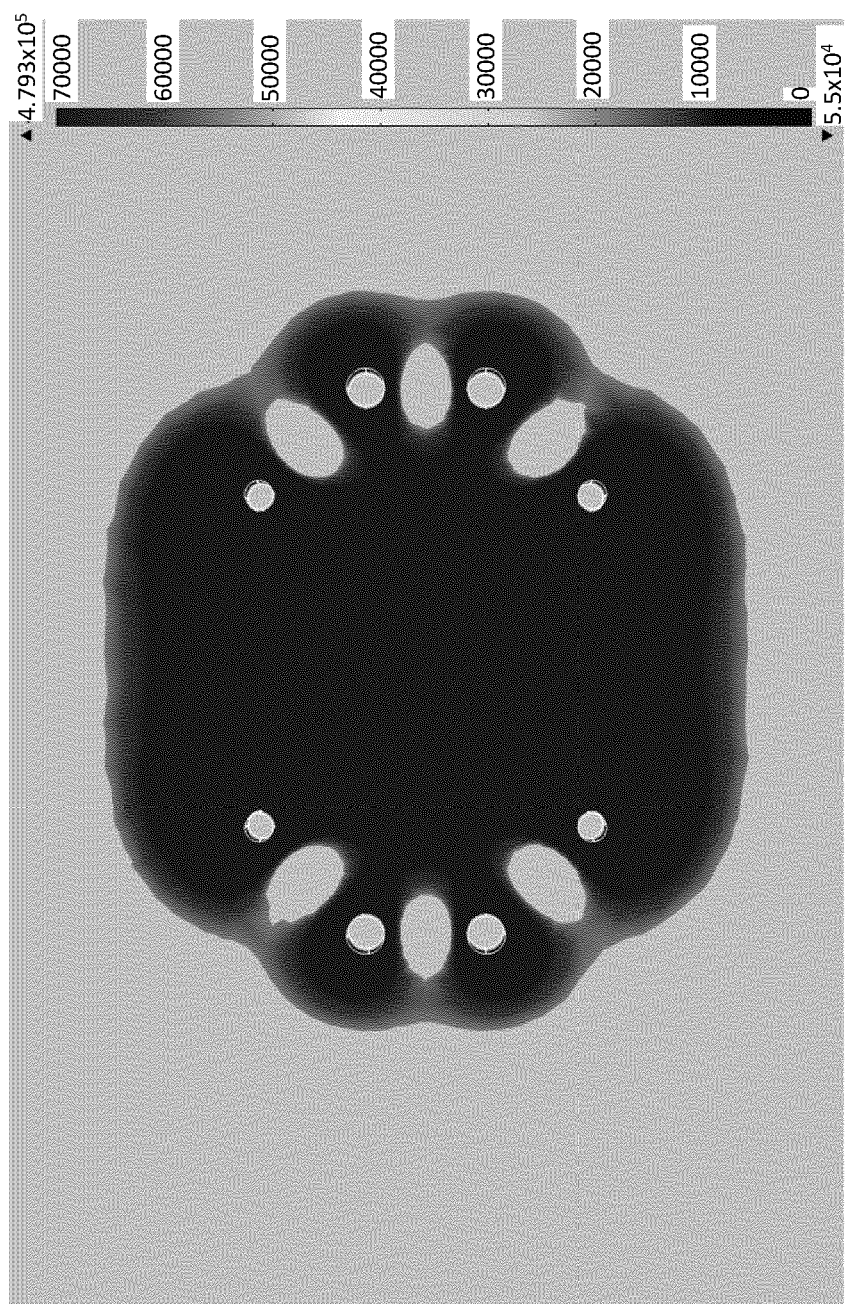
FIG. 12 shows electrical field calculation for an eight-needle version of the electrode assembly in which all electrode elements are not equidistant.

FIG. 12 shows electrical field calculation for a 8 electrode elements version of the electrode assembly, where first and ending needle are thinner, i.e. 0.15 mm radius, while the two central electrodes elements have a thickness of 0.2 mm radius.

The optimal layout applied to the eight-needle electrode assembly shows increased coverage compared to the reference layout. Non-equidistant and equidistant electrode element separations in each array show similar coverage.

Figure 13A:
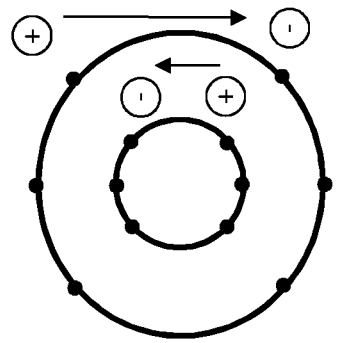
FIGS. 13A, 13B and 13C show concentric rings of electrode arrays using the offset central electrode element principle, according to some embodiments of the invention.
Figure 13C:
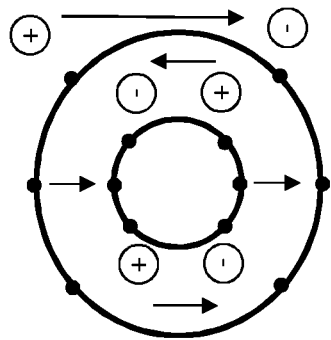
Figure 13B:
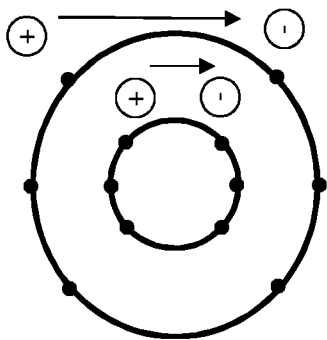

FIGS. 13A, 13B and 13C show concentric rings of electrode element arrays using the offset central electrode element principle.

The different polarity shown in the figures are examples of how the electrode assembly may be operated.

FIG. 14A and FIG. 14B show how perpendicular fields may be used in the electrode array set-up.

As shown in FIGS. 14A and 14B an electrode apparatus may comprise four arrays located in a cross configuration so that the bipolar arrangement may be switch between opposite array so as to achieve desired perpendicular electrical fields.

FIG. 15 shows a flow-chart of an electroporation method for creating one or more electrical fields to generate an electroporation and/or electrophoretic effect in a target tissue in a luminal organ.

The method comprises:
(S1) providing an electroporation assembly according to the first aspect of the invention;
(S2) inserting the endoscopic sheath through tissues of a body or into a luminal organ and bring into a vicinity of a target region to be treated, while the retractable electrode assembly is in a retracted position;
(S3) extending the retractable electrode assembly to an extended position to at least partially surrounding tissue in a target region to be treated; and
(S4) transmitting from the retractable electrode assembly one or more electric pulses of specific amplitudes and durations to create one or more electric fields in the target region.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An electrode apparatus comprising: an electrode assembly comprising a bipolar arrangement of an even number of arrays, wherein said even number of arrays comprises two or more arrays, wherein each one of said two or more arrays comprises one or more electrode elements; and wherein said two or more arrays have opposite polarity, when in operation; and wherein said electrode elements of each one of said two or more arrays are at least three electrode elements, and wherein said at least three electrode elements of each one of said two or more arrays comprises a first, one or more central and an ending electrode element, and said at least three electrode elements of each one of said two or more arrays are configured to produce an electric field having uniform intensity along an imaginary straight line between said first and said ending electrode element of said at least three electrode elements having the same polarity, said imaginary line connecting and crossing said first and said ending electrode element having the same polarity; and wherein said one or more central electrode element are offset of said imaginary straight line, thereby producing an electric field region having a square or rectangular shape cross section avoiding cold spots along said imaginary line, when in operation;

wherein said bipolar arrangement is a circular arrangement and wherein said first, one or more central and ending electrode element of each one of said two or more arrays are arranged on opposite locations of said bipolar arrangement; and wherein, when in operation, said at least three electrode elements of one of said two or more arrays have a positive polarity and said at least three electrode elements of one of said two or more arrays have a negative polarity and said at least three electrode elements having a positive polarity are arranged on the perimeter of a first half of said circular arrangement and said at least three electrode elements having a negative polarity are arranged on said perimeter of a second opposite half of said circular arrangement.

2. The electrode apparatus according to claim 1, wherein said imaginary straight line is an imaginary straight line between a tip of said first and a tip of said ending electrode element of said at least three electrode elements having the same polarity.

3. The electrode apparatus according to claim 1, wherein said electrode assembly is a retractable electrode assembly, and said electrode apparatus further comprises:
an endoscopic sheath; and wherein said retractable electrode assembly is configured for endoscopic use.

4. The electrode apparatus according to claim 1, wherein said one or more central electrode elements are offset by 0.75 and 1.75 mm from said imaginary straight line between said first electrode element and said ending electrode element of the at least three electrode elements having the same polarity.

5. The electrode apparatus according to claim 3, wherein said bipolar arrangement is an arrangement, wherein said two or more arrays surround an optical axis of said endoscopic sheath, and wherein said at least three electrode elements of each one of said two or more arrays are arranged along a perimeter of said bipolar arrangement.

6. The electrode apparatus according to claim 3, wherein said bipolar arrangement is a circular arrangement, wherein said at least three electrode elements of each one of said two or more arrays are circularly arranged around an optical axis of said endoscopic sheath.

7. The electrode apparatus according to claim 3, wherein said one or more central electrode element of each array of said at least three electrode elements having same polarity are located offset an imaginary chord between the first and the ending electrode elements of the at least three electrode elements having the same polarity, or wherein said at least three electrode elements of each one of said two or more arrays are arranged along a circumference of said circular arrangement.

8. The electrode apparatus according to claim 1, wherein said first, one or more central and ending electrode element of each one of said two or more arrays are arranged on opposite locations of said bipolar arrangement.

9. The electrode apparatus according to claim 1, wherein said even number of arrays is four and wherein a first bipolar arrangement of two arrays having positive polarity and negative polarity and a second bipolar arrangement of two arrays having positive polarity and negative polarity are located along a circumference of one or more separated concentric rings.

10. The electrode apparatus according to claim 1, further comprising an electric pulse generator, and wherein said electric pulse generator supplies single electrical pulses or sequence of electrical pulses according to an electroporation protocol for drug or gene delivery, or wherein said electric pulse generator supplies single electrical pulses or a sequence of electrical pulses according to an irreversible electroporation protocol.

11. The electrode apparatus according to claim 1, wherein said electrode elements are needle shaped electrode elements.

12. The electrode apparatus according to claim 1, wherein said electrode elements are needle shaped electrode elements having needle shaped tips.

13. The electrode apparatus according to claim 1, wherein said electrode elements are needle shaped electrode elements having round shaped tips.

14. The electrode apparatus according to claim 1, wherein said first, one or more central and ending electrode elements are a number of first, one or more central and ending electrode elements.

15. The electrode apparatus according to claim 3, wherein said bipolar arrangement is a circular arrangement, wherein said two or more arrays surround the optical axis of said endoscopic sheath.

16. The electrode apparatus according to claim 1, wherein said one or more electrode elements are at least six electrode elements having tips having sharp outer surface geometry.

17. The electrode apparatus according to claim 16, wherein said at least six electrode elements have tips comprising a blunt or rounded outer surface geometry.

18. The electrode apparatus according to claim 1, wherein said electrode assembly has a cross section in a range between 40 and 1 mm.

19. The electrode apparatus according to claim 3, wherein said endoscopic sheath is a resectoscope.

20. An electroporation method for creating one or more electrical fields to generate an electroporation and/or electrophoretic effect in a target tissue in a luminal organ, said method comprising:
  providing an electrode apparatus according to claim 1;
  inserting the electrode assembly through a tissue of a body of a subject via insertion of a cannula or sheath or into a luminal organ by endoscope and bring into a vicinity of a target region to be treated, while said retractable electrode assembly is in a retracted position;
  extending said retractable electrode assembly to an extended position to at least partially surrounding tissue in a target region to be treated; and
  transmitting from said retractable electrode assembly one or more electric pulses of specific amplitudes and durations to create one or more electric fields in said target region further comprising administering a dose of a therapeutic molecule through said endoscopic sheath, while or before applying through said electrode assembly said one or more pulses.

21. An electrode apparatus comprising:
an electrode assembly comprising a bipolar arrangement of an even number of arrays, wherein said even number of arrays comprises two or more arrays, wherein each one of said two or more arrays comprises one or more electrode elements; and
wherein said two or more arrays have opposite polarity, when in operation; and
wherein said electrode elements of each one of said two or more arrays are at least three electrode elements, and wherein said at least three electrode elements of each one of said two or more arrays comprises a first, one or more central and an ending electrode element, and said at least three electrode elements of each one of said two or more arrays are configured to produce an electric field having uniform intensity along an imaginary straight line between said first and said ending electrode element of said at least three electrode elements having the same polarity, said imaginary line connecting and crossing said first and said ending electrode element having the same polarity; wherein said bipolar arrangement is a circular arrangement and wherein said first, one or more central and ending electrode element of each one of said two or more arrays are arranged on opposite locations of said bipolar arrangement; and
wherein, when in operation, said at least three electrode elements of one of said two or more arrays have a positive polarity and said at least three electrode elements of one of said two or more arrays have a negative polarity and said at least three electrode elements having a positive polarity are arranged on the perimeter of a first half of said circular arrangement and said at least three electrode elements having a negative polarity are arranged on said perimeter of a second opposite half of said circular arrangement; and
wherein said one or more central electrode element are offset of said imaginary straight line, thereby, when in operation, producing an electric field region having a square or rectangular shape cross section avoiding cold spots along said imaginary line.

* * * * *